US010456538B2

(12) United States Patent
Dellaca et al.

(10) Patent No.: US 10,456,538 B2
(45) Date of Patent: Oct. 29, 2019

(54) METHOD AND SYSTEM FOR THE ADMINISTRATION OF A PULMONARY SURFACTANT BY ATOMIZATION (71) Applicant: Chiesi Farmaceutici S.p.A., Parma (IT)

(72) Inventors: Raffaele Dellaca, Milan (IT); Ilaria Milesi, Milan (IT)

(73) Assignee: Chiesi Farmaceutici S.p.A., Parma (IT)

(*) Notice: Subject to any disclaimer, the term of this patent is extended or adjusted under 35 U.S.C. 154(b) by 1580 days.

(21) Appl. No.: 13/868,436

(22) Filed: Apr. 23, 2013

(65) Prior Publication Data
US 2013/0333695 A1 Dec. 19, 2013

(30) Foreign Application Priority Data

Apr. 23, 2012 (EP) .................................... 12165234

(51) Int. Cl.
*A61M 15/00* (2006.01)
*A61M 11/02* (2006.01)
(Continued)

(52) U.S. Cl.
CPC ........... *A61M 15/009* (2013.01); *A61B 5/036* (2013.01); *A61B 5/4836* (2013.01); *A61M 11/02* (2013.01);
(Continued)

(58) Field of Classification Search
CPC ......... A61B 5/036; A61B 5/087; A61B 5/091; A61B 5/4836; A61B 5/7242;
(Continued)

(56) References Cited

U.S. PATENT DOCUMENTS 4,535,766 A 8/1985 Baum
4,813,431 A 3/1989 Brown
(Continued)

FOREIGN PATENT DOCUMENTS

DE 10 2010 025 045 12/2011
EP 0 692 273 1/1996
(Continued)

OTHER PUBLICATIONS

European Search Report in Application No. 12165234.1, dated Sep. 27, 2012.
(Continued)

*Primary Examiner* — Bradley H Philips
(74) *Attorney, Agent, or Firm* — Oblon, McClelland, Maier & Neustadt, L.L.P.

(57) ABSTRACT

A method and system according to preferred embodiments of the present invention allows optimizing the dispensing of aerosol medicaments. In particular the system according to a preferred embodiment of the present invention allows the administration of an exogenous pulmonary surfactant to very young patients (e.g. preterm neonates). A catheter 101 conveys atomized surfactant directly to the retro-pharyngeal region in order to increase efficiency of the medicament administration without being invasive: this is particularly important for very young patients, such as pre-term born neonates suffering from neonatal Respiratory Distress Syndrome (nRDS). According to a preferred embodiment of the present invention the catheter is made of biocompatible flexible material (e.g. plastic material). It is possible to couple the catheter with a rigid scaffolding (e.g. metallic) to increase stiffness of the device and to improve easiness of positioning operations. In a preferred embodiment of the present invention the delivery of the atomized medicament is done by means of an air blasting technique.

14 Claims, 10 Drawing Sheets (51) Int. Cl.
   *A61M 11/06* (2006.01)
   *A61M 15/08* (2006.01)
   *A61B 5/03* (2006.01)
   *A61B 5/00* (2006.01)
   *A61M 16/00* (2006.01)
   *A61M 16/04* (2006.01)
   *A61B 5/087* (2006.01)
   *A61B 5/091* (2006.01)
   *A61M 25/00* (2006.01)
   *A61M 16/10* (2006.01)

(52) U.S. Cl.
   CPC ........ *A61M 11/06* (2013.01); *A61M 15/0091* (2013.01); *A61M 15/08* (2013.01); *A61M 16/0057* (2013.01); *A61M 16/021* (2017.08); *A61M 16/0484* (2014.02); *A61M 16/0486* (2014.02); *A61B 5/087* (2013.01); *A61B 5/091* (2013.01); *A61B 5/7242* (2013.01); *A61M 16/0461* (2013.01); *A61M 16/107* (2014.02); *A61M 25/003* (2013.01); *A61M 2016/0021* (2013.01); *A61M 2016/0027* (2013.01); *A61M 2025/004* (2013.01); *A61M 2202/0488* (2013.01); *A61M 2205/3348* (2013.01); *A61M 2210/005* (2013.01); *A61M 2210/065* (2013.01); *A61M 2210/0618* (2013.01); *A61M 2240/00* (2013.01)

(58) Field of Classification Search
   CPC .... A61M 11/02; A61M 11/06; A61M 15/009; A61M 15/0091; A61M 15/08; A61M 16/00; A61M 16/0057; A61M 16/0461; A61M 16/0484

See application file for complete search history.

(56) References Cited

U.S. PATENT DOCUMENTS

| | | | |
|---|---|---|---|
| 5,577,496 A * | 11/1996 | Blackwood | A62B 18/006 |
| | | | 128/201.25 |
| 2005/0229926 A1 | 10/2005 | Fink et al. | |
| 2008/0000470 A1 | 1/2008 | Minocchieri et al. | |
| 2009/0199848 A1 | 8/2009 | Sharratt | |

FOREIGN PATENT DOCUMENTS

| | | | |
|---|---|---|---|
| EP | 1 426 057 | 6/2004 | |
| WO | 95/30448 | 11/1995 | |
| WO | WO 0047623 A1 * | 8/2000 | ........... C07K 14/785 |
| WO | 01/23025 | 4/2001 | |

OTHER PUBLICATIONS

International Search Report issued in PCT/EP2013/057744 dated May 24, 2013.
Office Action issued in European Patent Application No. 13715253.4 dated Dec. 16, 2015.
International Preliminary Report on Patentability and Written Opinion dated Oct. 28, 2014 in PCT/EP2013/057744.

* cited by examiner

METHOD AND SYSTEM FOR THE ADMINISTRATION OF A PULMONARY SURFACTANT BY ATOMIZATION

CROSS REFERENCES TO RELATED APPLICATIONS

This application claims priority to European Patent Application No. 12165234.1, filed on Apr. 23, 2012, which is incorporated herein by reference in its entirety.

BACKGROUND OF THE INVENTION

Field of the Invention

The present invention relates to the field of retropharyngeal instillation of a medicament and particularly to a method and system for the administration of a pulmonary surfactant by atomization.

Discussion of the Background

Administration of a medicament in the lungs is often faced with the problem of finding the right balance between the efficacy and the invasiveness of the treatment. This is particularly difficult with infants (hereinafter the term neonates is used as synonymous of infants). Preterm neonates may be affected by nRDS (neonatal Respiratory Distress Syndrome), a lung disease due to generalized immaturity which causes the lack of pulmonary surfactant. For many years, nRDS has been treated by administration of exogenous pulmonary surfactants as bolus through endotracheal instillation to the intubated pre-term neonates kept under mechanical ventilation. Although this treatment is very effective, as proven by the reduced mortality, it may present some drawbacks which are intrinsic to the mechanical ventilation (volu/barotrauma) and to the intubation procedure which is anyway invasive.

In view of the potential complications associated with intubation and mechanical ventilation, attention has been focused on different approaches of administration of exogenous pulmonary surfactants. In particular, as a possible respiratory support, use of non-invasive ventilation procedures such as early nasal Continuous Positive Airway Pressure (nCPAP), that delivers air into the lungs through specifically designed nasal devices such as masks, prongs or tubes, has been introduced in neonatal intensive care.

Following this orientation, in the last fifteen years great attention has also been paid to finding an alternative way for pulmonary surfactant administration. Most of the performed studies have been focused on the administration of nebulized surfactant (i.e. particles with a mass diameter<10 µm) by means of commercial nebulizers connected to the ventilator circuit, based on the hypothesis that a gentler and more gradual administration should prevent the high cerebral blood fluctuation that may occur with bolus administration (See e.g. Mazela J, Merrit T A, Finner N N "Aerosolized surfactants" Curr Opin Pediatr. 2007; 19(2): 155; or Mazela J, Polin R A "Aerosol delivery to ventilated newborn infants: Historical challenges and new directions" Eur J Pediatr. 2011:1-12; or Shah S "Exogenus surfactant: Intubated present, nebulized future?" World Journal of Pediatrics. 2011; 7(1): 11-5, both of which are incorporated herein by reference in their entireties). Albeit the surfactant results more homogenously distributed, the improvements in the lung functionalities obtained in the different studies are very contrasting and they do not evidence the effectiveness of the nebulization approach. In other studies surfactant nebulization system was connected to non-invasive ventilator settings (i.e. CPAP through nasal prongs); in these conditions the amount of nebulized surfactant that reached the lung appeared to be negligible (less than 20%). Moreover nebulized surfactant administered during CPAP has no conclusive beneficial impacts on lung functionality as shown in pilot studies on preterm neonates (see e.g. Berggren E, Liljedhal M, Winbladh B, Andreasson B, Curstedt T, Robertson B, et al "Pilot study of nebulized surfactant therapy for neonatal respiratory distress syndrome" Acta Paediatrica 2000; 89 (4): 460-4; or Firmer N N, Merritt T A, Bernstein G, Job L, Mazela J, Segal R "An open label, pilot study of Aerosurf combined with nCPAP to prevent RDS in preterm neonates" Journal of aerosol medicine and pulmonary drug delivery. 2010; 23(5): 303-9; or Jorch G, Hartl H, Roth B, Kribs A, Gortner L, Schaible T, et al "Surfactant aerosol treatment of respiratory distress syndrome in spontaneously breathing premature infants" Pediatr Pulmonol. 1997; 24(3): 222-4, all of which are incorporated herein by reference in their entireties). The studies are very variable and the authors apply different conditions with reference to several parameters, e.g.: 1) placement and type of aerosol generator, 2) mode of ventilation, 3) humidity, 4) air flow, 5) particle size, 6) nRDS models, 7) surfactant dilution, etc. Therefore it is difficult to make a proper comparison among them. However known systems do not generally prove to be very effective.

Moreover, when an aerosolized surfactant is administered with a nebulizer through a mask and not synchronized with the neonate' breath, some part can be exhaled during expiration and either deposits into the upper airways or tubing/connections or it is exhaled by the expiratory limbs. Moreover, the delivery of nebulised surfactant adds dead-space to the breathing circuits and, considering that preterm newborns may have a tidal volume of 1 ml or even less, this can promotes $CO_2$ retention that, eventually, could become dangerous if a final situation of hypercapnia is achieved.

An interesting approach that could partially mitigate the above risk has been proposed by Wagner et al (Wagner M H, Amthauer H, Sonntag J, Drenk F, Eichstädt H W, Obladen M "Endotracheal surfactant atomization: an alternative to bolus instillation?" Crit Care Med. 2000; 28(7):2540, which is incorporated herein by reference in its entirety) showing encouraging results. It is based on a modified tracheal tube with an atomizer inserted at the tip of the tube which produces particles, that have a SMD (Souter Mean Diameter)>100 µm, only during inspiration (identified by an operator). The choice of putting the atomizer directly into the tube has been technologically challenging.

The promising results of the Wagner approach are probably due to the bigger dimensions of the particles which allow the distribution and absorption of the pulmonary surfactant similar to the mechanisms involved in the bolus administration. In particular, it can be hypothesized that big particles will deposit on more central airways, being able to reach the non-expanded alveoli by diffusion gradient, Marangoni effect and capillarity, while, on the contrary, the small nebulized particles, which are able to pass through the upper airways, are likely to be either exhaled during expiration or being deposited into the already opened alveoli which produces the airflow during breathing, without reaching the attelectatic region of the lung and contributing to an even more inhomogeneous distribution of lung time constants. Another advantage of Wagner is that the pulmonary surfactant is administered during inspiration phase only and this helps in better controlling the quantity of medicament effectively delivered (with improvements in terms of saving and clinical results).

A drawback of Wagner is that the tube must reach the trachea (where the nebulizer is placed), in order to be able to deliver the big sized particles which would be filtered out by the upper airways, and this procedure is invasive and can cause problems, in particular for neonates. On the other hand, all known prior art systems implementing a non-invasive (i.e. not entering the tracheal tube) delivery method are capable of administering only small sized particles which are able to overcome the outer barrier, but are less efficient in reaching all the lung regions needing treatment.

Furthermore, according to Wagner's experiment, the "synchronization" of the delivery of medicament with the inspiration rhythm is done manually, which is not ideal for obvious reasons including a waste of the product. On the other hand all attempts known in the art for implementing such synchronization, for example those described in EP 692 273, which is incorporated herein by reference in its entirety, depend on the presence of devices such as a mechanical ventilator. However, this solution needs connections to the airway of the newborn, adding dead space and mechanical load to the patient's breathing.

For all these reasons, an improved non-invasive method and system for administering the exogenous surfactant which is capable of combining the advantages of big size particle nebulization with proper automatic synchronization of the delivery would be greatly appreciated.

SUMMARY OF THE INVENTION

Accordingly, it is one object of the present invention to overcome at least some of the problems associated with the prior art.

It is another object of the present invention to provide novel methods and systems for the administration of a pulmonary surfactant by atomization.

These and other objects, which will become apparent during the following detailed description, have been achieved by the inventors' discovery that a system for delivering a medicament to spontaneously breathing patients, comprising:
  i) a flexible catheter adapted to reach the retro-pharyngeal region of the patient, the catheter including at least a first channel being adapted to convey in the patient's pharyngeal region a flow of liquid medicament and at least a second channel adapted to convey in the patient's pharyngeal region a pressurized flow of gas;
  ii) first pump means connected to a first end of the at least first channel, adapted to create a pressure which pushes the column of liquid medicament towards the second end of the at least first channel; and second pump means connected to a first end of the at least second channel, adapted to create the flow of pressurized gas; so that when the column of liquid medicament and the pressurized gas meet in the pharyngeal cavity, the liquid column is broken into a plurality of particles causing the atomized medicament to be delivered into the patient's lungs; and
  iii) a pressure sensor connected to the at least first channel for measuring a value indicative of the pressure in the patient pharyngeal cavity, such value being use to determine whether the patient is in an inspiration or in an expiration phase and wherein the first pump means are selectively activated only during inspiration phase is effective for delivering a pulmonary surfactant.

Thus, according to one aspect of the present invention, the present invention provides a system for delivering a medicament to spontaneously breathing patients, comprising:
  i) a flexible catheter adapted to reach the retro-pharyngeal region of the patient, the catheter including at least a first channel being adapted to convey in the patient's pharyngeal region a flow of liquid medicament and at least a second channel adapted to convey in the patient's pharyngeal region a pressurized flow of gas;
  ii) first pump means connected to a first end of the at least first channel, adapted to create a pressure which pushes the column of liquid medicament towards the second end of the at least first channel; and a second pump means connected to a first end of the at least second channel, adapted to create the flow of pressurized gas; so that when the column of liquid medicament and the pressurized gas meet in the pharyngeal cavity, the liquid column is broken into a plurality of particles causing the atomized medicament to be delivered into the patient's lungs; and
  iii) a pressure sensor connected to the at least first channel for measuring a value indicative of the pressure in the patient pharyngeal cavity, such value being use to determine whether the patient is in an inspiration or in an expiration phase and wherein the first pump means are selectively activated only during inspiration phase.

The use of the liquid-filled lumen of the catheter for estimating the pressure swings at the pharyngeal cavity allows specific advantages compared to other approaches: 1) it provides a very fast response of the catheter-pressure transducer system (liquids are not compressible and adds a minimal compliance of the measuring system, resulting in very fast time constants), allowing a fast detection of the newborns breathing phase (respiratory rate in small preterm neonates can be greater than 60 breaths per minute, one order of magnitude greater than for adults); 2) the use of small and low-cost disposable catheters with no extra lumens for pressure sampling and with the pressure transducer being placed close to the main device; 3) the presence of liquid in the lumen prevents the tip of the catheter to be occluded by the fluids always present in the pharynx, for example saliva or moist due to the water vapor saturated environment, an important advantage against air-filled lumens for pressure sensing; 4) as the pressure swing due to the low-resistance pathway provided by the liquid-filled lumen is small compared to the gas ones, it is much easier to detect the very small pressure swings in the pharyngeal cavity due to breathing of the neonate, which are on the order of 1 cmH$_2$O.

Preferably the catheter is made of flexible plastic material and as an alternative it can include partially rigid scaffolding. Preferably the at least second channel includes a plurality of channels arranged around the first channel.

Preferably, the aerosol medicament comprises an exogenous pulmonary surfactant, e.g. selected from the group consisting of modified natural pulmonary surfactants (e.g. poractant alfa), artificial surfactants, and reconstituted surfactants, while the pressurized gas includes air or oxygen.

According to a further embodiment, the catheter includes spacers means arranged on its external surface so that, when the catheter is in place for the aerosol treatment, the second end of the at least first and at least second channel are kept separated from the wall of the pharyngeal cavity.

In a second embodiment, the present invention provides a method for preventing and/or treating a respiratory distress syndrome in spontaneously breathing patients, said method comprising the step of delivering an atomized medicament to the retro-pharyngeal region of the patient by means of a multi-channel flexible catheter a low pressure column of liquid medicament through at least a first channel of the multi-channel catheter and an pressurized flow of gas through at least a second channel of the multi-channel catheter; wherein the liquid column of medicament is broken into a plurality of particles when the liquid column and the pressurized flow of gas meet in the retro-pharyngeal cavity. Preferably the method comprises the step of detecting the inspiration activity of the patient, preferably by means of a pressure sensor being connected to the at least first channel; wherein the step of providing is performed only during the inspiration activity.

More preferably, the method of the invention comprises applying to the patient a non-invasive ventilation procedure such as nasal Continuous Positive Airway Pressure (nCPAP).

In a third embodiment, the present invention provides a kit comprising:
 a) a pharmaceutical composition comprising a pulmonary surfactant suspended in a pharmaceutically acceptable aqueous medium;
 b) the system of the invention;
 c) means for positioning and/or facilitating the introduction of the catheter into the retro-pharyngeal region; and
 d) container means for containing the pharmaceutical composition, the system and the positioning means.

In a fourth embodiment, the present invention provides a method for preventing and/or treating a respiratory distress syndrome in spontaneously breathing pre-term neonates, said method comprising the step of delivering a pulmonary surfactant in the retro-pharyngeal cavity of said neonates.

A still further aspect of the present invention provides a computer program for controlling the above described method.

The method and system according to preferred embodiments of the present invention allow optimizing the dispensing of surfactant with an efficient delivery of the atomized particles to the lungs without requiring an invasive operation for placing the catheter. The method and system of the present invention provides several advantages including: a more gentle atomizing process, thanks to the air-blasting atomizing catheter, whose mechanical impact on the surfactant is minimal; an easier manufacturing and a more compact design of the atomizing catheter thanks to the absence of the ending taper; the possibility to monitor and to synchronize to the breathing pattern of the patient without the introduction of a sensor, connections at the airway opening or a second lumen; the flexibility of the device, which can be used either during spontaneous breathing or when non-invasive respiratory support is provided, such as during nCPAP or other non-invasive ventilation procedures such as nasal intermittent positive-pressure ventilation (NIPPV); the use of components which are already familiar to the hospital personnel, e.g. catheters and disposable pressure sensors (similar to the ones used for invasive monitoring of blood pressures); all the part in contact with the pulmonary surfactant and the patient are low cost and disposable, granting for hygienically and safer treatments than those of the prior art, which is particularly important when the patient is a pre-term neonate.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

With the term "pulmonary surfactant" it is meant an exogenous pulmonary surfactant administered to the lungs that could belong to one of the following classes:
 (i) "modified natural" pulmonary surfactants which are lipid extracts of minced mammalian lung or lung lavage. These preparations have variable amounts of SP-B and SP-C proteins and, depending on the method of extraction, may contain non-pulmonary surfactant lipids, proteins or other components. Some of the modified natural pulmonary surfactants present on the market, like Survanta™ are spiked with synthetic components such as tripalmitin, dipalmitoylphosphatidylcholine and palmitic acid.
 (ii) "artificial" pulmonary surfactants which are simply mixtures of synthetic compounds, primarily phospholipids and other lipids that are formulated to mimic the lipid composition and behavior of natural pulmonary surfactant. They are devoid of pulmonary surfactant proteins;
 (iii) "reconstituted" pulmonary surfactants which are artificial pulmonary surfactants to which have been added pulmonary surfactant proteins/peptides isolated from animals or proteins/peptides manufactured through recombinant technology such as those described in WO 95/32992, which is incorporated herein by reference in its entirety, or synthetic pulmonary surfactant protein analogues such as those described in WO 89/06657, WO 92/22315, and WO 00/47623, all of which are incorporated herein by reference in their entireties.

The term "non-invasive ventilation (NIV) procedure" defines a ventilation modality that supports breathing without the need for intubation.

Figure 1:
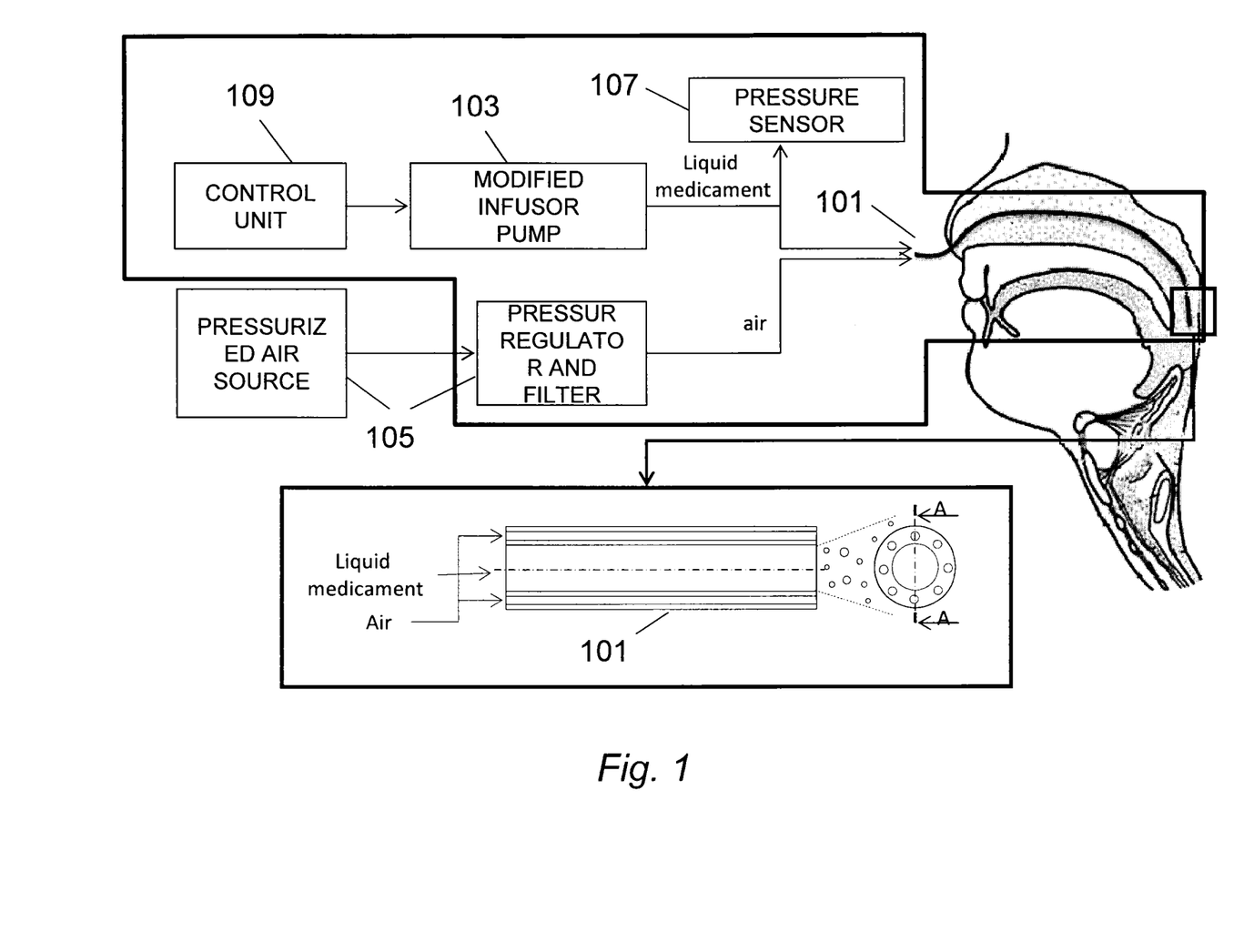
FIG. 1 is a schematic diagram of the system implementing a preferred embodiment of the present invention.

With reference to FIG. 1 an implementation of the method and system according to a preferred embodiment of the present invention is illustrated. In the example here discussed the problem of delivering the right amount of atomized medicament to a patient is addressed: in particular a pulmonary surfactant (e.g. poractant alfa, commercially available as Curosurf™ from Chiesi Farmaceutici SpA) is administered to e.g. a preterm neonate.

However, any pulmonary surfactant currently in use, or hereafter developed for use in respiratory distress system and other pulmonary conditions could be suitable for use in the present invention. These include modified natural, artificial and reconstituted pulmonary surfactants (PS).

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf™, Chiesi Farmaceutici SpA, Parma, Italy), and beractant (Survanta™, Abbott Laboratories, Inc., Abbott Park, Ill.)

Examples of artificial surfactants include, but are not limited to, pumactant (Alec™, Britannia Pharmaceuticals, UK), and colfosceril palmitate (Exosurf™, GlaxoSmithKline, plc, Middlesex).

Examples of reconstituted surfactants include, but are not limited to, lucinactant (Surfaxin™, Discovery Laboratories, Inc., Warrington, Pa.) and the product having the composition disclosed in Table 2 of Example 2 of WO 2010/139442, whose teaching is incorporated herein by reference in its entirety.

Preferably, the pulmonary surfactant is a modified natural surfactant or a reconstituted surfactant. More preferably the pulmonary surfactant is poractant alfa (Curosurf™).

The dose of the pulmonary surfactant to be administered varies with the size and age of the patient, as well as with the severity of the patient's condition. Those of skill in the relevant art will be readily able to determine these factors and to adjust the dosage accordingly.

A catheter 101 conveys atomized medicament (e.g. surfactant) directly to the retro-pharyngeal region in order to increase efficiency of the medicament administration without being invasive: this is particularly important for very young patients, such as pre-term born neonate suffering from neonatal Respiratory Distress Syndrome (nRDS). According to a preferred embodiment of the present invention the catheter is made of biocompatible flexible material (e.g. plastic material). It is possible to couple the catheter with a rigid scaffolding (e.g. metallic) to increase stiffness of the device and to improve easiness of positioning operations. In a preferred embodiment of the present invention the delivery of the atomized medicament is done by means of an air blasting technique. Using air to assist atomization is a well known technique that grants a fully developed atomization also when low pressure and low flow conditions are required (see e.g. Arthur Lefebvre, "Atomization and spray", Taylor and Francis, 1989, which is incorporated herein by reference in its entirety). Such technique is based on a relatively small amount of gas (e.g. air, but it could be other compressed gas, e.g. oxygen, nitrogen, or helium) which flows in one or more separate channels than the medicament which is delivered in a liquid form; the air flow accelerates and breaks the liquid column, inducing the atomization of the medicament. Therefore the catheter 101 includes a plurality of channels (at least two, one for the medicament and one for the air) for conveying contemporarily the medicament and the air flow. The liquid medicament column is broken up in droplets by the turbulence due to the air flowing next or around when the two flows (air and liquid medicament) exit the catheter channels and meet in the retro-pharyngeal region. The atomized droplets have a mean diameter of at least 80 microns, preferably higher than 100 microns, more preferably of 80 to 150 microns. It is believed that this effect is caused by the air flow which accelerates the fluid sheet instability. The air also helps in dispersing the droplets, preventing collision among them and facilitating the diffusion of the medicament in the lungs by reducing the likelihood of contact between the particles and the wall of the retropharyngeal cavity.

In a preferred embodiment of the present invention the medicament (e.g. the surfactant) is supplied by means of a pump 103 connected to one end of the catheter, which forces the liquid medicament out of the opposite end of the catheter where it meets the air flow (conveyed by a different channel of the catheter) and is atomized, i.e. broken into a plurality of small particles (droplets) by the pressurized air. Pump 103 may be realized by a device able to generate a flow, such as an infusion pump: in a preferred embodiment of the present invention the pump 103 is made of a mechanical frame comprising a structure that holds a syringe containing the liquid medicament and a stepper motor that pushes the syringe piston. In an embodiment of the present invention, pump 103 can be controlled by a control unit 109; such control unit can be embodied in a computer, a microprocessor or, more generally any device capable of data processing activity. A pump device 105 (possibly including a pressurized source and pressure regulator and filter) is connected to the one or more channel conveying the air flow. Those skilled in the art will appreciate that the term pump includes any device capable of providing a pressure to either a liquid flow or a flow of gas. Pump 105 can be controlled by a control unit, as described for the pump 103. The flow of the pump 103 should be in the range of 9 to 18 ml/H while the pressure of the pump 105 should be comprised between 0.4 and 0.8 Atm (1 Atm=1.01325 Bar).

Figure 2A:
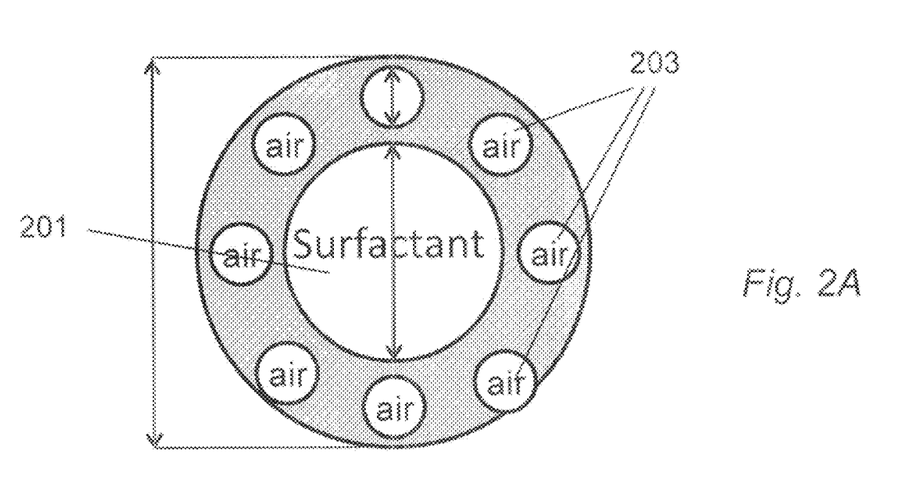
FIGS. 2A and 2B show an example of multi channel catheter according to an embodiment of the present invention.
Figure 2B:
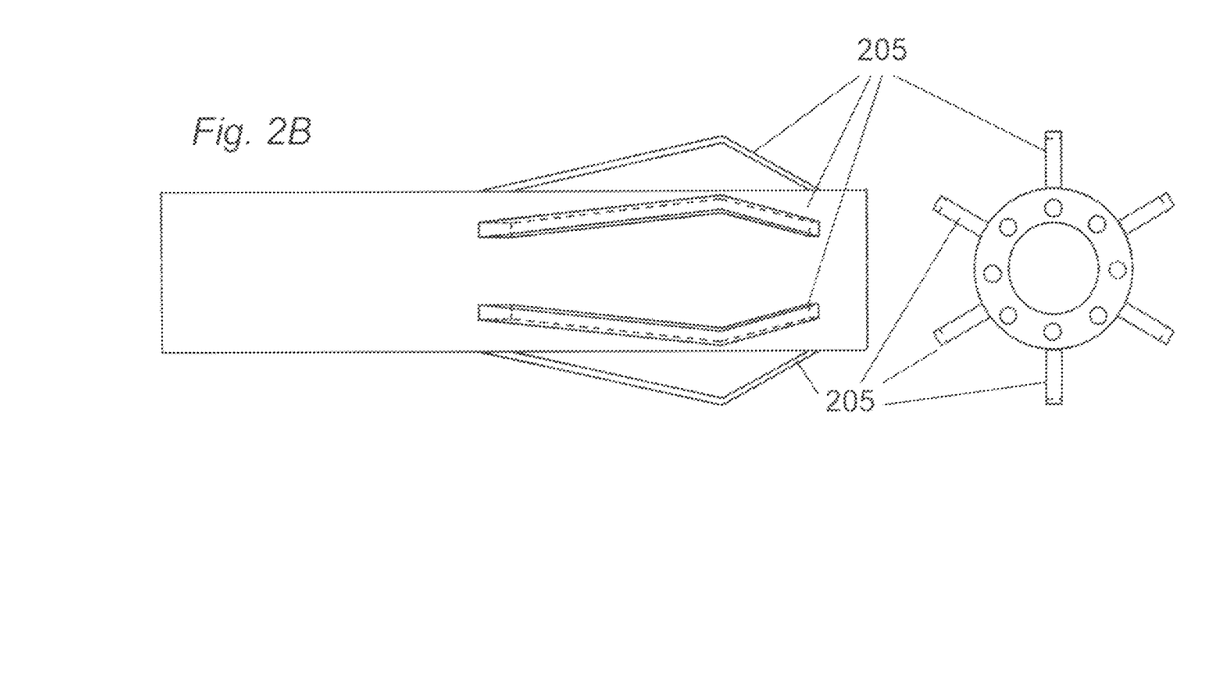
Figure 3:
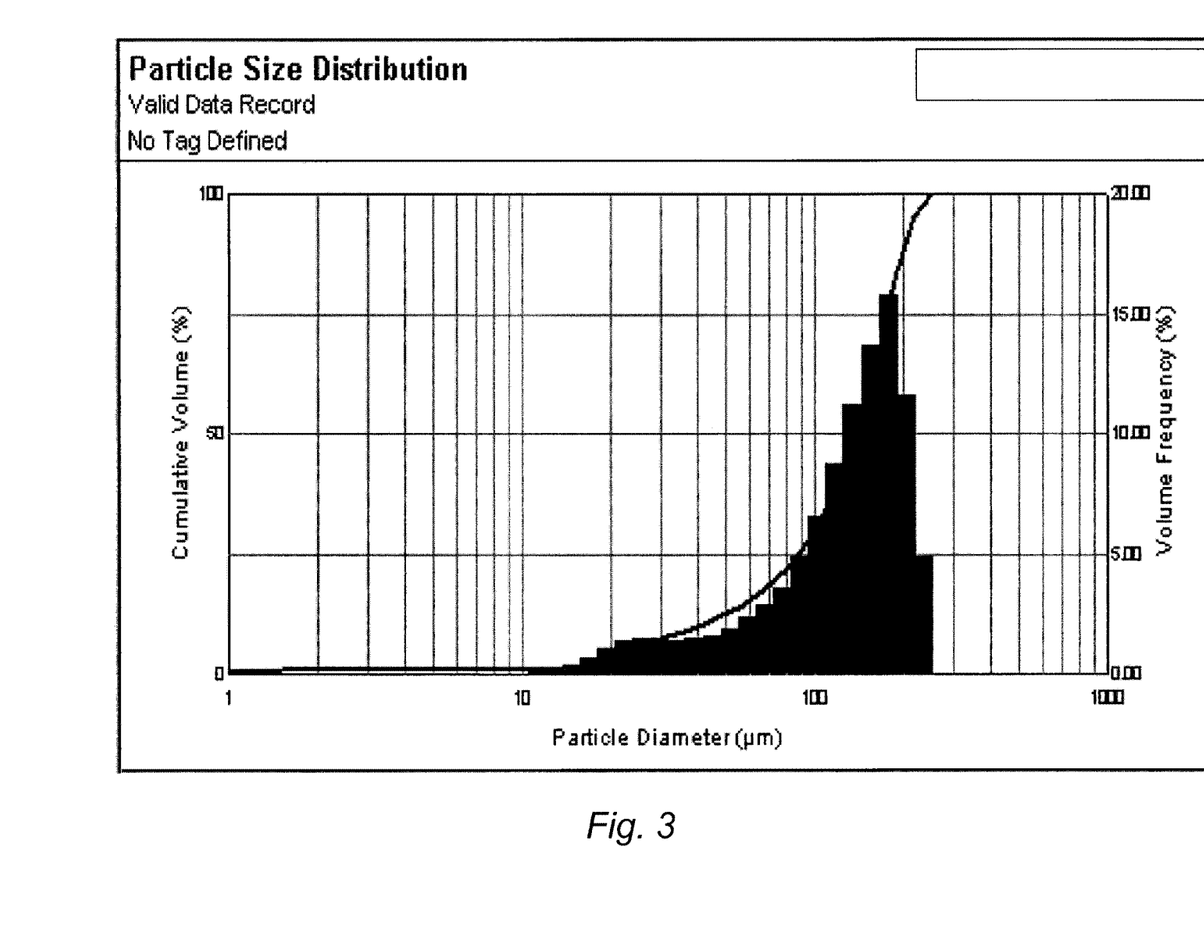
FIG. 3 shows as example the particles dimension of surfactant (Curosurf™) atomized according to the preferred embodiment of the present invention.
Figure 4A:
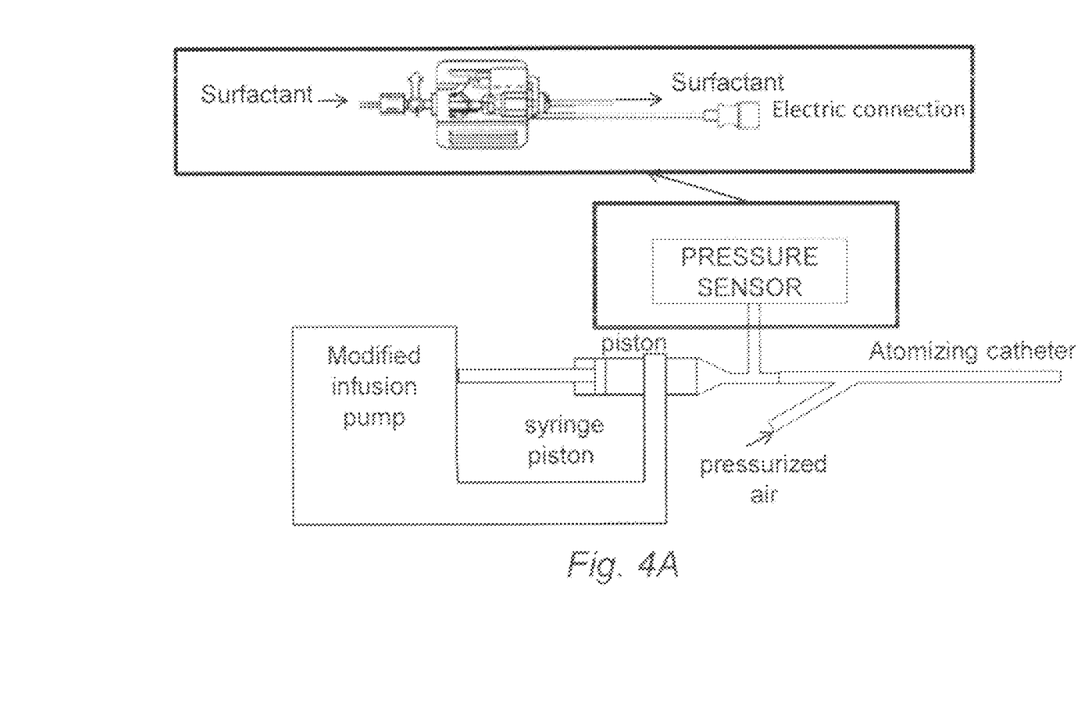
FIGS. 4A and 4B represent respectively a pressure sensor according to an embodiment of the present invention and the circuit controlling the pressure sensor.
Figure 4B:
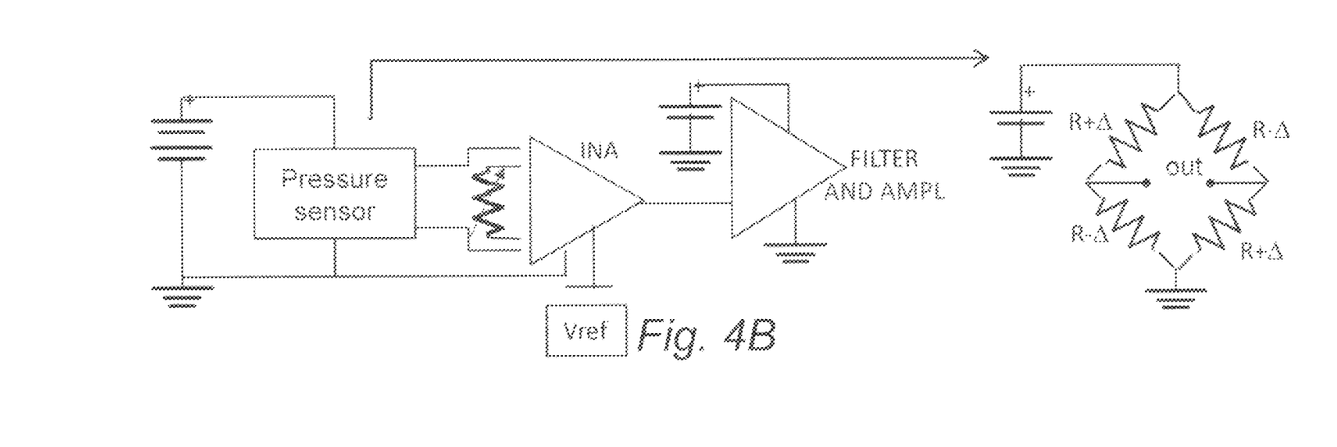

In a preferred embodiment of the present disclosure the catheter 101 includes multiple channels, with a main (e.g. central) channel conveying the surfactant, being surrounded by a plurality of additional channels (e.g. lateral) which convey a pressurized air flow). The air blasting technique here described provides the advantage of a more gentle fragmentation of the surfactant. Current atomizers for drug delivery are normally based on plain orifices, while the method according to the present disclosure employs an atomizing catheter using the air blasting approach. The geometrical configuration of the plain orifice normally presents a narrowing at the tip of the catheter, the nozzle, which accelerates the liquid producing an high instability in presence of an high pressure drop (more than 1 Atm) and, as a consequence, the fragmentation of the liquid in particles. On the contrary, the air blasting catheter according to a preferred embodiment of the present disclosure is a multi-lumen catheter: the surfactant flows into the main lumen while pressurized air flows in the lateral ones. The turbulences generated by the small airflow fragment the surfactant in a very 'gentle' way. Moreover, the use of plain orifices would require very high differential pressure across the nozzle to induce atomization, while the air blasting atomizer doesn't need high driving pressure to the surfactant, as the atomizing process is driven by the turbulence of the air around the surfactant.

The pulmonary surfactant is preferably administered as a suspension in a sterile pharmaceutically acceptable aqueous medium, preferably in a buffered physiological saline (0.9% w/v sodium chloride) aqueous solution.

Its concentration shall be properly adjusted by the skilled person in the art.

Advantageously, the concentration of the surfactant is 2 to 160 mg/ml, preferably 10 to 100 mg/ml, more preferably 40 to 80 mg/ml.

The applied volume should generally be not more than 5.0 ml, preferably not more than 3.0 ml. In some embodiments, it could be 1.5 ml or 3 ml.

A possible additional feature of the method and system according to the present invention is that of synchronizing the pulmonary surfactant administration with the breathing phase of the patient. To implement this feature, a pressure sensor 107 is inserted along the surfactant catheter, but externally to the pharyngeal tube, and provides an indirect but accurate measurement of the pharyngeal pressure swings. This measurement is possible because of the relatively low pressure in the channel conveying the surfactant, allowing the use of the surfactant line for measuring the retro-pharyngeal pressure with the aim of both synchronizing the atomization with the breathing pattern of the patients and to help the attending medical staff to place the catheter in the proper place and monitoring the maintenance of the proper position during the treatment, allowing the identification of wrong positioning of the catheter tip (e.g. into the oesophagus).

FIG. 2 shows a specific implementation of the multichannel catheter according to a preferred embodiment of the present invention. The air blasting atomizer of the present embodiment is realized by means of a multi-lumen catheter with a central inner lumen 201 surrounded by several smaller lumens 203. The surfactant flows into the main central lumen, driven by the infusion pump, while the gas (e.g. air, oxygen-enriched air or pure oxygen), flows through the lateral lumens. The pressure drop in the central catheter depends on its length and internal diameter. In a preferred embodiment of the present disclosure the catheter could present a length of 7 to 15 cm and an internal diameter of 0.4 to 0.6 mm. In this case the pressure drop is in the range of 7.8 to 0.72 $cmH_2O$, considering a flow of surfactant of 3 mL/20 min. In this way a nozzle is not required and the particles size dimension is determined mainly by the pressure of the air which flows in the lateral channel. To generate the gas flow into the lateral lumens a compressor or a pressurized gas source (e.g. a cylinder or a medical gas wall plug) can be used: the pressure is modulated by a pressure regulator with a mechanical filter to avoid dust flowing through the system.

Such pressurized gas flow is not able to significantly alter the pressure in the pharynx, since the flow is rather limited and the anatomical structures are open to the atmosphere.

The distribution of the particles size obtained by means of the preferred embodiment of the present invention has been characterized by a commercial laser diffractive size analyzer (Malvern, Insitec RT). The measurements have been carried out using exemplificative conditions of 0.5 bar of pressurized air and a surfactant flow rate of 3 mL/20 minutes.

As a result, the most of the particles size is comprised between 100 to 200 microns. In particular the median value is 137.47 micron, the $10^{th}$ percentile is 39.50 micron, the $90^{th}$ percentile is 130.63 micron as reported in FIG. 3.

In one embodiment, the catheter contains a single channel or lumen for the surfactant having an inner diameter of about 0.25 mm, surrounded by 12 channels or lumen for air each having an inner diameter of about 0.12 mm, which leads to a ratio of the area of the surfactant channel to the total area of the air channels of about 0.4. Of course, other diameters may be used. For example, in another embodiment, the surfactant channel may have an inner diameter of about 0.2 mm to about 0.6 mm and the air channels may have inner diameters of about 0.05 mm to about 0.15 mm. In particular, the surfactant channel may have an inner diameter of about 0.5 mm and the air channels may have inner diameters of about 0.12 mm, which leads to a ratio of the area of the surfactant channel to the total area of the air channels of about 1.4. Of course, the catheter itself will have an outer diameter large enough to accommodate the surfactant and air channels.

As a possible additional feature, the catheter used in the method and system of the present invention could be provided with some spacers on the external surface which help in positioning it and keeping a minimum distance between the catheter itself and the wall of the retro-pharyngeal cavity. This separation ensures that the atomised surfactant is conveyed to the lung by inspiratory airflow and not projected on the walls of the pharyngeal cavity. An example is shown in FIG. 2*b* where some ribs are running along the external surface of the catheter; these ribs can also have a stiffening function adding some sort of rigidity to the catheter (as an alternative to the metal scaffolding mentioned above). Other shapes of the ribs are possible, e.g. they could be in the shape of one or more rings surrounding the catheter at predetermined distance one each other: those skilled in the art will appreciate that several equivalent alternatives can be implemented.

Laryngoscope is another tool known to the skilled person, that could be suitably utilized for positioning the catheter in the retro-pharyngeal cavity.

Moreover, Magill forceps, oro-pharyngeal cannulas such as cannula of Mayo, of Guedel, of Safar and of Bierman can facilitate the introduction of the catheter. In a preferred embodiment the cannula of Mayo is utilized for both facilitating the introduction and keeping the catheter tip in the proper position, i.e. not close to the pharyngeal wall and pointing toward the inlet of the trachea during the whole period of surfactant delivery.

FIG. 4*a* shows a possible implementation of the pressure sensor 107 mentioned above, which is used in an embodiment of the present invention to detect the pressure of the air coming from or flowing into the pharyngeal cavity. Such measured pressure is used as an indication of the breathing rhythm of the patient and the system synchronizes the administration of the medicament accordingly. This synchronization brings big advantages both in term of efficacy of the treatment and in reducing the waste of medicament. The efficacy is due to the transportation of the atomized drug by the inspiratory flow; the saving is caused by the fact that the medicament is delivered only when needed, avoiding to waste it while the patient is exhaling. In an embodiment of the present disclosure the pressure sensor is inserted along the surfactant line and transduces the pressure from the tip of the catheter (i.e. the pressure in the neonate pharynx) to the sensing element which acts as a variable resistance. When the motor is activated the syringe gently pushes the surfactant into the atomizing catheter to allow an averaged flow of 3 ml/h (this parameter can be adjusted on the treatment program). As shown in FIG. 4*b*, the sensor exploits the piezoresistive phenomenon to convert the mechanical pressure into a voltage drop; it has an internal Wheatstone Bridge connection, which means that it is internally compensated for ambient temperature fluctuations.

The sensor can be for example a disposable pressure sensor, similar to those used for the invasive measurement of blood pressure.

The administration of surfactant only during the inspiration phase is a big advantage provided by the present invention: this results in a better control on the effective quantity which reaches alveoli and to avoid the waste of the supplied surfactant. This requires the measurement of a signal related to the breathing pattern in the ventilatory condition of the preterm neonate (spontaneously breathing and kept under nCPAP or other non-invasive ventilation procedure such as NIPPV) to detect the end-inspiration and end-expiration and to predict the 'future' breathing pattern of the baby. According to an embodiment of the present invention, the administration of surfactant is started before the beginning of the inspiration and stopped before the beginning of the expiration in order to:
1) take into account the mechanical delays in the atomization;
2) prevent the loss of surfactant since the surfactant delivered at end inspiration will be still in the pharyngeal cavity and therefore exhaled during the beginning of the expiration.

Figure 5A:
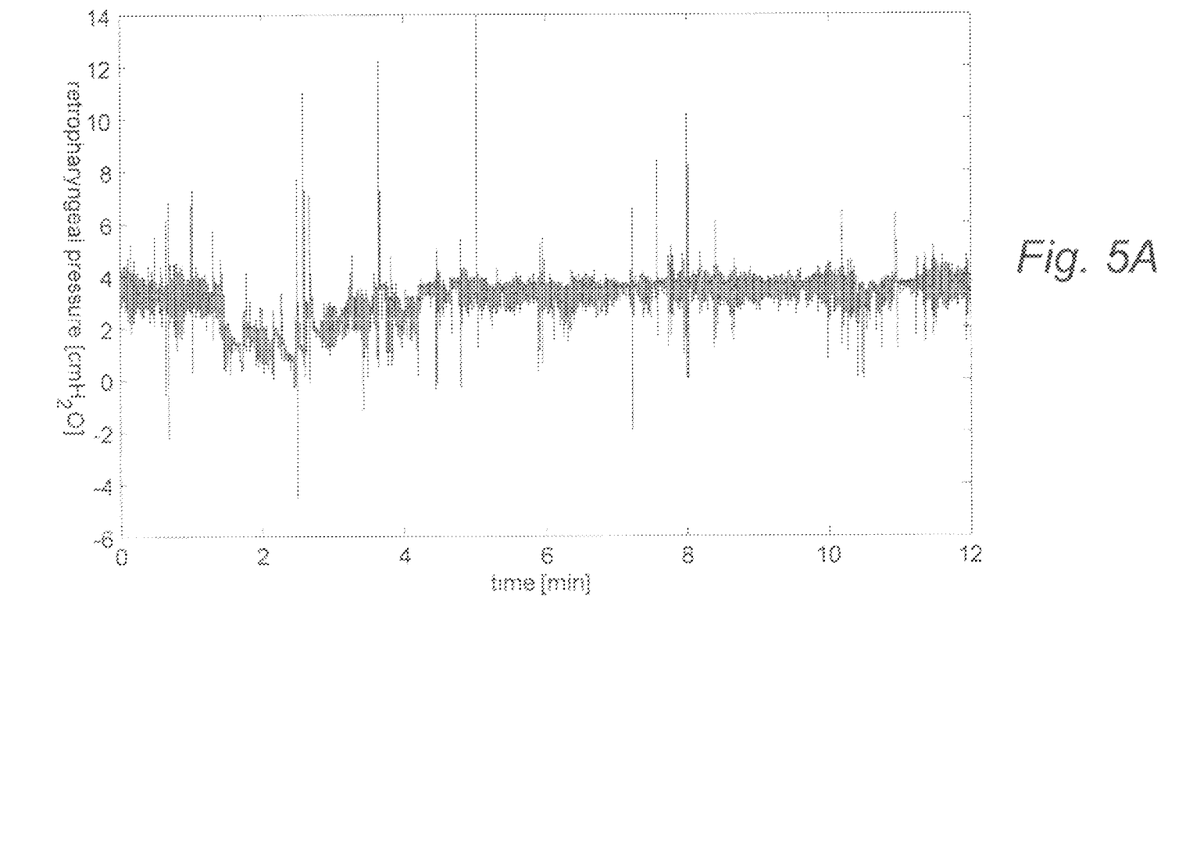
FIGS. 5A and 5B show an exemplificative retropharyngeal pressure signal acquired on a preterm neonate.
Figure 5B:
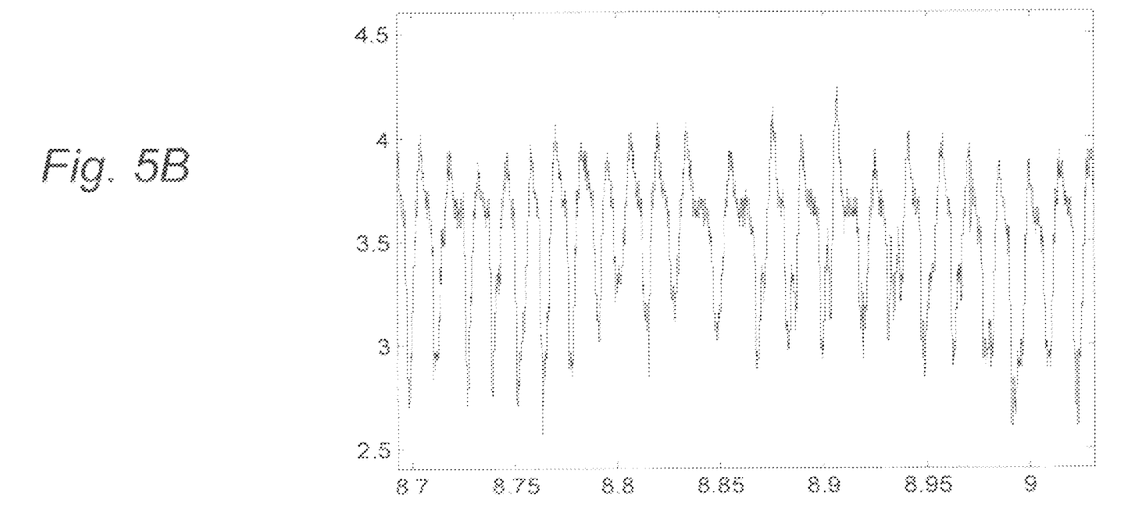
Figure 6:
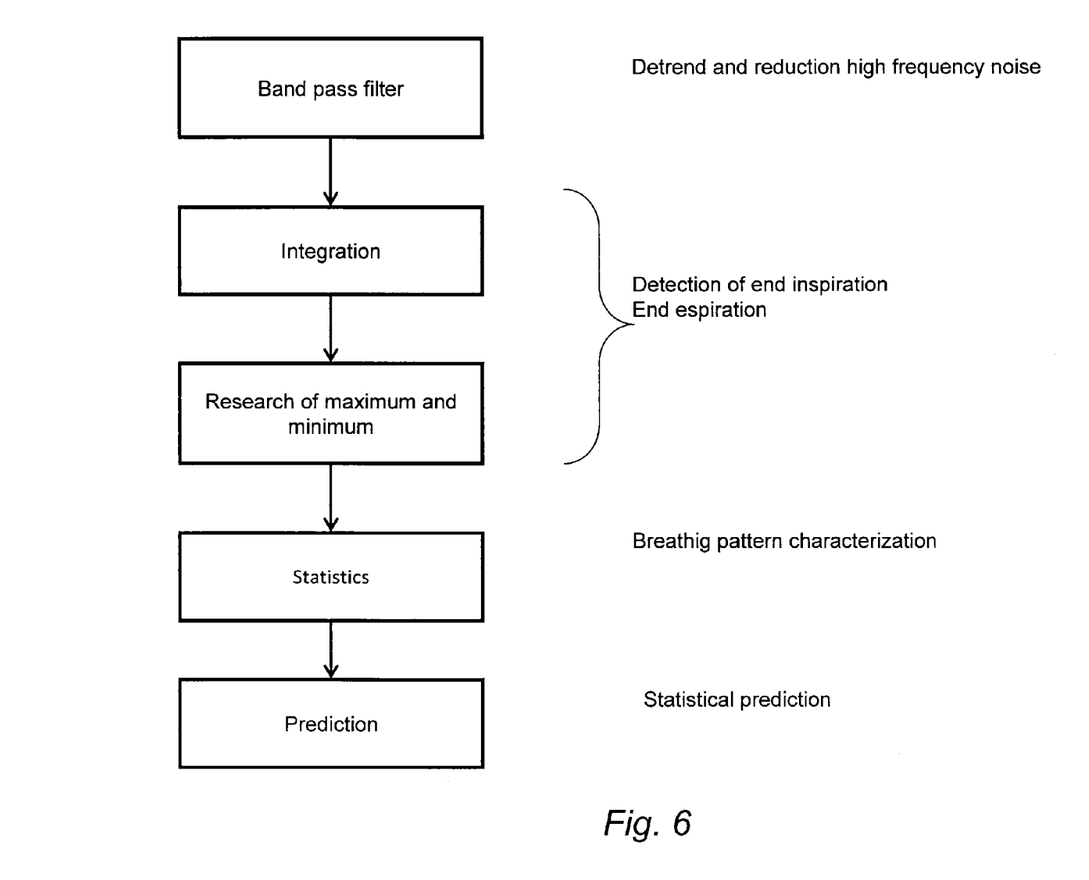
FIG. 6 shows the steps of the method according to a preferred embodiment of the present invention.

In FIG. 5 are reported retropharyngeal pressure tracings from a representative preterm baby with gestational age of 28 weeks and a body weight of 1650 g. Panel a shows the whole track characterized by a very high variability with several spikes and base line fluctuations; in panel b an enlargement of the same signal is reported. A statistical analysis on the data has been performed and a predictive algorithm has been designed. The main steps of which are reported in the flow chart of FIG. 6, with the relative functions. In particular, after the removal of trends and high frequency noise, the signal is integrated to obtain a new signal proportional to the lung volume, and by looking for maxima and minima it is possible to detect the end-inspiratory and end-expiratory points. Our statistical analysis includes also the measurement of the pressure involved, which is about 1 cmH$_2$O in all the different conditions.

By using this approach we have obtained in an exemplificative simulation, the administration of the 97±0.8% of surfactant in 60±21 minutes in 7 preterm neonates with a gestational age of 29.5±3 weeks and a body weight of 1614 g (±424 g).

All operations of the system here described are controlled by a microprocessor (e.g. microcontroller of PIC18F family by Microchip Technology Inc.) running a software adapted to implement the method according to a preferred embodiment of the present invention.

It will be appreciated that alterations and modifications may be made to the above without departing from the scope of the invention. Naturally, in order to satisfy local and specific requirements, a person skilled in the art may apply to the solution described above many modifications and alterations. Particularly, although the present invention has been described with a deep degree of particularity with reference to preferred embodiment(s) thereof, it should be understood that eventual omissions, substitutions and changes in the form and details as well as other embodiments are possible; moreover, it is expressly intended that specific elements and/or method steps described in connection with any disclosed embodiment of the disclosure may be incorporated in any other embodiment as a general matter of design choice.

For example, similar considerations apply if the components (e.g. microprocessor or computers) have different structure or include equivalent units; in any case, it is possible to replace the computers with any code execution entity (such as a PDA, a mobile phone, and the like).

Similar considerations apply if the program (which may be used to implement some embodiments of the disclosure) is structured in a different way, or if additional modules or functions are provided; likewise, the memory structures may be of other types, or may be replaced with equivalent entities (not necessarily consisting of physical storage media). Moreover, the proposed solution lends itself to be implemented with an equivalent method (having similar or additional steps, even in a different order). In any case, the program may take any form suitable to be used by or in connection with any data processing system, such as external or resident software, firmware, or microcode (either in object code or in source code). Moreover, the program may be provided on any computer-usable medium; the medium can be any element suitable to contain, store, communicate, propagate, or transfer the program. Examples of such medium are fixed disks (where the program can be preloaded), removable disks, tapes, cards, wires, fibres, wireless connections, networks, broadcast waves, and the like; for example, the medium may be of the electronic, magnetic, optical, electromagnetic, infrared, or semiconductor type.

In any case, the solution according to the present invention lends itself to be carried out with a hardware structure (for example, integrated in a chip of semiconductor material), or with a combination of software and hardware. The system of the invention is particularly suitable for the prevention and/or treatment of the respiratory distress syndrome (RDS) of the neonate (nRDS). However, it could be advantageously utilized for the prevention and/or treatment of adult/acute RDS (ARDS) related to a surfactant-deficiency or dysfunction as well as of conditions in which respiratory distress may be present as a consequence of, for instance, meconium aspiration syndrome, pulmonary infection (e.g. pneumonia), direct lung injury and bronchopulmonary dysplasia.

Advantageously, the system of the invention is applied to pre-term neonates who are spontaneously breathing, and preferably to extremely low birth weight (ELBW), very-low-birth-weight (VLBW), and low-birth weight (LBW) neonates of 24 to 35 weeks gestational age, showing early signs of respiratory distress syndrome as indicated either by clinical signs and/or supplemental oxygen demand (fraction of inspired oxygen (FiO$_2$)>30%).

More advantageously, nasal Continuous Positive Airway Pressure (nCPAP) is applied to said neonates, according to procedures known to the person skilled in the art.

Preferably a nasal mask or nasal prongs are utilized. Any nasal mask commercially available may be used, for example those provided by The CPAP Store LLC, and the CPAP Company.

Nasal CPAP is typically applied at a pressure between 1 and 12 cm water, preferably 2 to 8 cm water, although the pressure can vary depending on the neonate age and the pulmonary condition.

Other non-invasive ventilation procedures such as nasal intermittent positive-pressure ventilation (NIPPV), High Flow Nasal Cannula (HFNC), and bi-level positive airway pressure (BiPAP) can alternatively be applied to the neonates.

Other features of the invention will become apparent in the course of the following descriptions of exemplary embodiments which are given for illustration of the invention and are not intended to be limiting thereof.

EXAMPLES

In vivo efficacy of atomized surfactant (in this example poractant alfa, as defined above) was evaluated in preterm newborn rabbits at the 27th day of gestation (term=31±1 days). The model chosen closely resembles the conditions of premature babies affected by RDS in that the lungs of these animals are not yet able to produce their own surfactant, but can warrant gas exchange so that they can expand in response to exogenous surfactant administration.

Treatments were intratracheally given at 2 ml/kg volume, corresponding to 160 mg/kg dose. Foetuses, paralyzed with pancuronium bromide (0.02 mg i.p.), were then placed in the plethysmograph system at 37° C. and ventilated with pure oxygen at constant pressure (frequency 40/minute, inspiration/expiration ratio 60/40). No positive end-expiratory pressure (PEEP) was applied. An "opening" pressure of 35 cmH$_2$O was first applied for 1 minute to overcome initial resistance due to capillarity in finer conducting airways. It was then followed by 15 minutes at 25 cmH$_2$O, 5 minutes at 20 cmH$_2$O, 5 minutes at 15 cmH$_2$O and again at 25 cmH$_2$O for the final 5 minutes.

Respiratory flow was measured every 5 minutes by a Fleish tube connected to each chamber of the plethysmograph system. Tidal volume (Vt) was automatically obtained by integration of the flow curve.

Two sets of experiments were performed.

In the first set, five samples (1 ml each) have been received. The pulmonary surfactant administered at each samples is respectively: not atomized poractant alfa, poractant alfa atomized at an air pressure of 0.0, 0.2, 0.5, and 0.8 bar. The pulmonary surfactant has been atomized using the preferred embodiment of the present invention.

In this set of experiments a control group without any treatment was included.

All the atomized samples, including that passed through without any pressure applied, resulted as effective as not atomized poractant alfa (P<0.05, one-way ANOVA followed by Tukey's test; Graphpad Prism). No statistically significant difference was found between the different conditions of atomization.

In the second set, three samples (1 ml each) have been received. The pulmonary surfactant administered at each samples is respectively: non-atomized poractant alfa, poractant alfa atomized at an air pressure of 0.2, 0.5, and 0.8 bar.

In this set of experiments two further groups were included, a control group without any treatment and a group treated with a batch of poractant alfa already released to the market.

The same results were observed in the second set of experiments.

Figure 7:
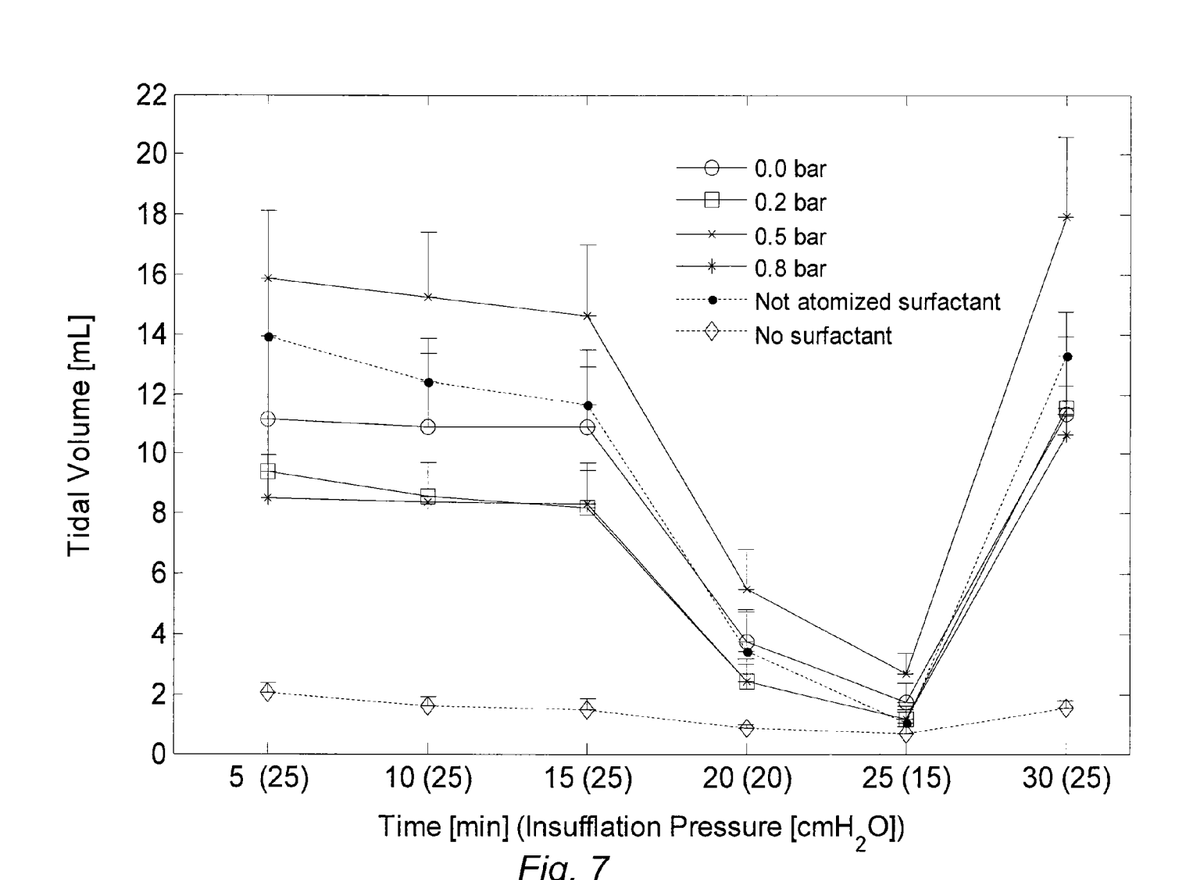
FIG. 7 shows a diagram of tidal volume related to fetuses being treated with the method and system according to an embodiment of the present invention.

As the results were consistent in the two sets, the data have been pooled (FIG. 7). Statistical analysis of these data confirmed the previous results.

In conclusion the passage through the atomizer, using the preferred embodiment of this invention, does not affect poractant alfa efficacy in premature rabbit foetuses. In particular, atomization at pressures between 0.2 and 0.8 bar does not significantly affect poractant alfa efficacy and the application of 0.5 bar seems the most suitable although no statistically significant difference has been observed between different atomization conditions.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A system configured to deliver an atomized medicament to a spontaneously breathing pre-term neonate, the system comprising:
    a flexible catheter sized such that a distal end portion thereof is provided in the retro-pharyngeal region of the spontaneously breathing pre-term neonate, the flexible catheter including at least a first channel that outputs into the spontaneously breathing pre-term neonate's pharyngeal cavity a flow of liquid medicament, and at least one second channel that outputs into the spontaneously breathing pre-term neonate's pharyngeal cavity a pressurized flow of gas;
    a first pump connected to a first end of the first channel, that creates a low pressure which pushes a column of liquid medicament toward a second end of the first channel;
    a second pump connected to a first end of each said at least one second channel, that creates the pressurized flow of gas;
    so that when the column of liquid medicament and the pressurized flow of gas meet in the pharyngeal cavity, the column of liquid medicament is broken into a plurality of particles by the pressurized flow of gas, causing atomization of the liquid medicament and the atomized medicament to be delivered into the spontaneously breathing pre-term neonate's lungs;
    a controller that controls at least the first pump; and
    a pressure sensor, connected to the first channel, that measures a value indicative of pressure in the pharyngeal cavity of the spontaneously breathing pre-term neonate, such value being used by the controller to determine whether the spontaneously breathing pre-term neonate is in an inspiration or in an expiration phase,
    wherein the first pump is selectively activated by the controller only during the inspiration phase.

2. A system according to claim 1, wherein said at least one second channel includes a plurality of second channels arranged around the first channel.

3. A system according to claim 1, wherein said flexible catheter is made of flexible plastic material.

4. A system according to claim 3, wherein said flexible catheter includes a partially rigid scaffolding.

5. A system according to claim 1 wherein said flexible catheter includes a plurality of spacers arranged on an external surface thereof so that, when the flexible catheter is in place for delivering the atomized medicament, the second end of the first channel and the at least one second channel are kept separated from the wall of the pharyngeal cavity of the spontaneously breathing pre-term neonate.

6. A system according to claim 1, wherein the at least one second channel conveys pressurized air as the pressurized flow of gas.

7. A kit comprising:
    a medicament;
    the system according to claim 1;
    a device that positions and/or facilitates the introduction of the flexible catheter into the retro-pharyngeal region of the spontaneously breathing pre-term neonate; and
    a container the contains the liquid medicament, the system, and the device that positions and/or facilitates the introduction of the flexible catheter.

8. A system according to claim 1, wherein droplet size of the atomized medicament is from 80 to 200 microns in diameter.

9. A system according to claim 1, wherein the controller controls output of from 1.5 ml to 5.0 ml of liquid medicament in the column of liquid medicament per treatment session.

10. A system according to claim 1,
    wherein the pressure sensor is connected to the first channel, wherein the pressure sensor is external to the distal end portion of the flexible catheter that is to be provided in the retro-pharyngeal region of the spontaneously breathing pre-term neonate, and wherein the pressure sensor is arranged to indirectly measure pharyngeal pressure swings.

11. A system according to claim 1, wherein a diameter of the first channel is greater than a diameter of each said at least one second channel.

12. A system according to claim 1, wherein the distal end portion of the flexible catheter is free of a nozzle.

13. A system according to claim 1, wherein the inspiration phase is defined as starting before the beginning of inspiration and stopping before the beginning of expiration.

14. A system according to claim 1, wherein the controller predicts a future breathing pattern of the spontaneously breathing pre-term neonate for use as the inspiration phase.

\* \* \* \* \*